US008636136B2

(12) United States Patent
Schoultz

(10) Patent No.: US 8,636,136 B2
(45) Date of Patent: Jan. 28, 2014

(54) APPARATUS AND METHOD FOR ROTATABLY CONVEYING AND APPLYING DISCRETE PARTS TO A SUBSTRATE

(75) Inventor: Adam N. Schoultz, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 110 days.

(21) Appl. No.: 13/332,234

(22) Filed: Dec. 20, 2011

(65) Prior Publication Data

US 2013/0153365 A1 Jun. 20, 2013

(51) Int. Cl.
*B65G 47/244* (2006.01)
(52) U.S. Cl.
CPC .................................... *B65G 47/244* (2013.01)
USPC ................ 198/471.1; 198/474.4; 198/377.08; 156/519; 156/552; 156/164
(58) Field of Classification Search
USPC ......... 198/377.01–377.09, 458, 471.1, 803.5; 156/519, 540–541, 552, 556, 164; 414/776
See application file for complete search history.

(56) References Cited

U.S. PATENT DOCUMENTS

| | | | |
|---|---|---|---|
| 3,215,250 A * | 11/1965 | Schubert | 198/377.04 |
| 3,386,558 A * | 6/1968 | Benatar | 198/408 |
| 4,608,115 A | 8/1986 | Schroth et al. | |
| 4,610,751 A | 9/1986 | Eschler | |
| 4,726,876 A | 2/1988 | Tomsovic, Jr. | |
| 5,025,910 A | 6/1991 | Lasure et al. | |
| 5,091,039 A | 2/1992 | Ujimoto et al. | |
| 5,224,405 A | 7/1993 | Pohjola | |
| 5,556,504 A | 9/1996 | Rajala et al. | |
| 5,660,665 A | 8/1997 | Jalonen | |
| 5,716,478 A | 2/1998 | Boothe et al. | |
| 5,746,869 A | 5/1998 | Hayden et al. | |
| 5,759,340 A | 6/1998 | Boothe et al. | |
| 5,873,870 A | 2/1999 | Seitz et al. | |
| 6,022,443 A | 2/2000 | Rajala et al. | |
| 6,139,004 A | 10/2000 | Couillard et al. | |
| 6,319,347 B1 | 11/2001 | Rajala et al. | |
| 6,523,595 B1 | 2/2003 | Milner et al. | |
| 6,524,423 B1 | 2/2003 | Hilt et al. | |
| 6,550,517 B1 | 4/2003 | Hilt et al. | |
| 6,589,149 B1 | 7/2003 | VanEperen et al. | |
| 6,599,384 B2 | 7/2003 | Milner et al. | |
| 6,620,276 B1 | 9/2003 | Kuntze et al. | |
| 6,656,312 B1 | 12/2003 | Schmitz et al. | |
| 6,722,494 B2 | 4/2004 | Nakakado | |
| 6,748,996 B2 | 6/2004 | Nakakado et al. | |
| 6,766,843 B2 | 7/2004 | Hilt et al. | |

(Continued)

FOREIGN PATENT DOCUMENTS

EP    0 950 624 A2    10/1999
JP    2006-124045 A    5/2006

(Continued)

*Primary Examiner* — Mark A Deuble
(74) *Attorney, Agent, or Firm* — Patrick C. Wilson

(57) ABSTRACT

An apparatus for conveying a plurality of parts to a substrate in a configuration which is offset from the centerline of the supply feed of discrete parts is disclosed as well as the related process. Such an apparatus and process are suitable for use in the production of products where one or more components of the product must be spatially shifted from their incoming location relative to the movement of the assembly line to a second position which is offset from its incoming location and orientation.

12 Claims, 5 Drawing Sheets

(56) References Cited

U.S. PATENT DOCUMENTS

| | | |
|---|---|---|
| 6,899,780 B2 | 5/2005 | Rajala et al. |
| 6,915,829 B2 | 7/2005 | Popp et al. |
| 6,942,086 B2 * | 9/2005 | Bridges et al. .......... 198/377.08 |
| 6,976,521 B2 | 12/2005 | Mlinar et al. |
| 7,000,755 B2 * | 2/2006 | van Pinxteren et al. ...... 198/374 |
| 7,008,497 B2 | 3/2006 | Nakakado et al. |
| 7,195,684 B2 | 3/2007 | Satoh |
| 7,216,685 B2 | 5/2007 | Nakakado et al. |
| 7,220,335 B2 | 5/2007 | Van Gompel et al. |
| 7,341,087 B2 | 3/2008 | Tabor et al. |
| 7,398,870 B2 | 7/2008 | McCabe |
| 7,438,779 B2 | 10/2008 | Nakakado |
| 7,721,872 B2 | 5/2010 | Aoyama et al. |
| 7,770,712 B2 | 8/2010 | McCabe |
| 7,975,584 B2 | 7/2011 | McCabe |
| 7,987,964 B2 | 8/2011 | McCabe |
| 2003/0010603 A1 * | 1/2003 | Corrigan .................... 198/474.1 |
| 2004/0245069 A1 * | 12/2004 | Hook et al. ................ 198/459.1 |
| 2005/0067093 A1 | 3/2005 | Goda et al. |
| 2005/0082141 A1 * | 4/2005 | Dombek .................... 198/474.1 |
| 2006/0157188 A1 | 7/2006 | Thorson et al. |
| 2007/0074953 A1 * | 4/2007 | McCabe ................. 198/377.08 |
| 2007/0142805 A1 | 6/2007 | Gompel et al. |
| 2010/0243155 A1 | 9/2010 | Andrews |
| 2011/0212818 A1 | 9/2011 | Nakakado et al. |

FOREIGN PATENT DOCUMENTS

| | | |
|---|---|---|
| WO | WO 97/24283 A1 | 7/1997 |
| WO | WO 2004/004618 A1 | 1/2004 |
| WO | WO 2007/039800 A1 | 4/2007 |

* cited by examiner

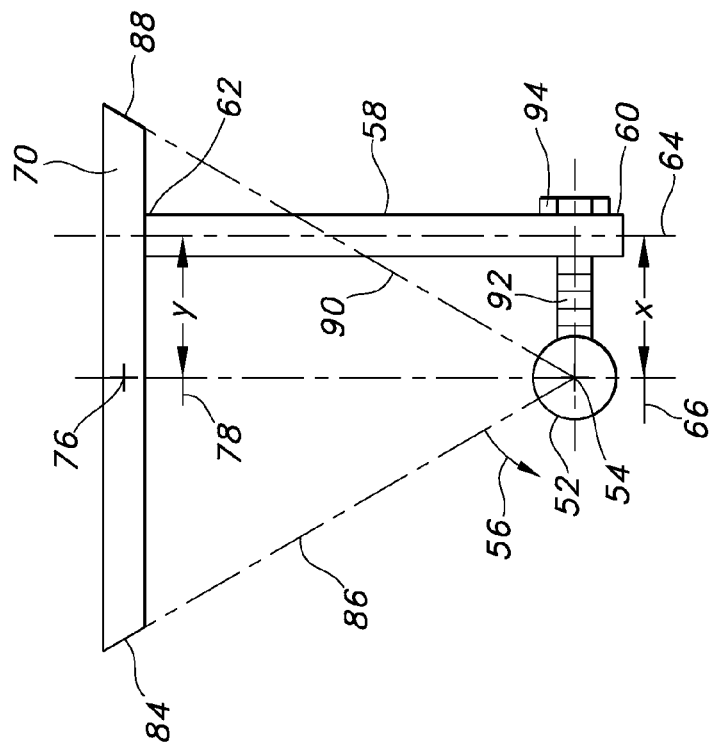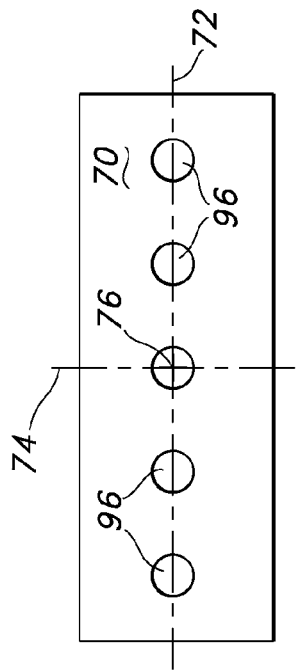

APPARATUS AND METHOD FOR ROTATABLY CONVEYING AND APPLYING DISCRETE PARTS TO A SUBSTRATE

FIELD OF THE INVENTION

The field of the invention relates generally to web treatment apparatus and more specifically to apparatus for conveying a plurality of discrete parts and applying the plurality of discrete parts to a substrate in an offset configuration as well as a method of using the apparatus.

BACKGROUND OF THE INVENTION

Disposable absorbent articles such as diapers, diaper pants, training pants, incontinence garments and pads as well as feminine hygiene products including sanitary napkins, panty liners and the like are in wide use today by a wide variety or users including infants, children and adults. As a result, manufacturers of such products must invest large amounts of capital in the machinery and methods for making such products. This is especially true due to the large number of variations and sizes for each of the products that are required to satisfy the consumer needs. As a result, there is a need for the equipment used to make these products to be as versatile as possible.

When making such products, it is not unusual for there to be dozens of components that go into the final product. To make these products, it is common for individual components to be cut from stock material, either on line or off line and then fed into a main forming line to mate with other components of the end product. Mating and indexing these components, especially at the very high speeds at which such machines run, is often a detailed process. In some instances the components being combined are traveling at the same speed while in other instances, one component is moving faster or slower than the others. As a result, one component must be sped up or slowed down to ensure proper indexing and attachment to yield a quality product both as to function and aesthetics. Thus there is a need for equipment and processes that will accommodate such variability in design.

One particular problem is encountered when a component being introduced into the production line is not in the proper orientation with respect to how it is to ultimately be fitted to the overall product. As a result, much effort has been put forth in designing equipment and processes that will allow some portion or portions of the product or components to be rotated from a first position or orientation into a second position or orientation to properly align with the finished product. In the context of the main manufacturing line, the travel of the product down the production line is typically referred to as the machine direction (MD) of movement and the direction at right angles to this direction is referred to as the cross-machine direction (CD). In many instances a component must be rotated 90 degrees in the same plane from the machine direction to the cross-machine direction or vice versa to properly align the component with the end product. In other situations in may be necessary to rotate a component or product to a lesser or greater degree such as, for example, 45 degree or 135 degrees to achieve a particular product design.

While there are many designs of equipment that accomplish this task, one design employs a series of rotating arms driven by a drive shaft. At the end of each of the arms is what is referred to as a transfer puck. Each of the pucks is designed to pick up a discrete piece of material and hold it with the use of a vacuum or other holding means. If need be, the individual arms can be sped up or slowed down if the substrate onto which the discrete parts are being deposited is not moving at the same speed. Once the piece is picked up by an individual puck it is then rotated to the proper orientation and then deposited onto the substrate. See for example, U.S. Pat. Nos. 5,716,478 and 5,759,340 both to Boothe et al. and 6,139,340 to Couillard et al.

When the component being deposited on the substrate is centered on the product and assembly line, this pick up, rotation and deposition process is rather simple. However, if the component must be skewed to a position that is offset from the normal line of travel of the conveying mechanism, problems arise. One solution is to physically shift the transfer equipment off the centerline of the production line and/or attempt to skew the incoming webs of material from the centerline of production. Both of these processes are cumbersome or pose problems such as web breakage and unacceptable downtimes to shift and realign equipment. As a result, there is a need for equipment and processes that will facilitate the application of offset components onto a moving web or substrate.

One example of an area where this is a particular problem is with products that are made in the cross-machine direction. Many disposable absorbent articles are made in the machine direction. By this it is meant that the longitudinal centerline of the product is parallel to the direction of movement of the assembly line and aligned with the longitudinal centerline of the assembly line. Thus, for example, if it is desired to shift or skew the position of a particular component of the end product, shifting the product is more a function of the sequential timing as to when the component is picked up, rotated and then laid down onto the assembly line. In some instances, however, the equipment is designed to make product where the longitudinal direction of the product is perpendicular to the direction of the assembly line. When this type of CD equipment is being used, shifting the location of a component can be more difficult. One example would be shifting the location of the absorbent core in a diaper or incontinence product towards the front of the product to accommodate the male anatomy. In such situations, it may be necessary to shift the incoming supply webs or stop the line to physically shift the application equipment off the centerline of the production line. A similar situation can arise when the product is being made in the machine direction but the product employs complimentary components that are equally spaced to either side of the centerline of the production equipment thus necessitating offset of the equipment to either side of the centerline.

The present invention employs a delivery and application system that allows individual components to be applied to a moving web or conveyor at an offset location from the centerline of the product and/or the production line thereby facilitating the creation of customized products that meet the particular needs of the end user.

SUMMARY

To overcome the foregoing problems, disclosed herein is an apparatus and process for conveying a plurality of parts and applying the parts to a moving substrate in an offset configuration from the centerline of the incoming supply of parts. In one embodiment, the conveying and transfer apparatus includes a rotation means defining a rotation axis with the rotation means having a first direction of rotation about the rotation axis such that the plurality of parts can be applied to the substrate. The apparatus can be fitted with a plurality of transfer arms each having a longitudinal transfer arm axis, a proximal end and a distal end. The plurality of transfer arms are attached to the rotation means in a radial pattern about the rotation means with each of the proximal ends of the transfer arms being attached to the rotation means in such a manner that the longitudinal transfer arm axis is offset from the rotation axis by a transfer arm offset distance. A plurality of transfer pucks are adapted to convey the parts to the substrate. Each of the transfer pucks has a longitudinal puck axis and a lateral puck axis which intersect at a center point on each of the plurality of transfer pucks. The distal ends of the transfer arms are attached to the transfer pucks at a location which is offset from the center point of the transfer pucks by a transfer puck offset distance. Each of the transfer pucks are configured to pivot about the longitudinal transfer arm axis so that each of the transfer pucks is pivotal between a first position wherein the transfer pucks are oriented to receive the parts and a second position wherein the transfer pucks are oriented to apply the parts to the moving substrate.

In another embodiment of the present invention, the apparatus defines a rotation axis and includes a rotation means with a plurality of transfer arms each attached to the rotation means in a radial pattern about the rotation means. Each of the transfer arms has longitudinal transfer arm axis, a proximal end and a distal end with the proximal ends being attached to the rotation means in such a manner that the longitudinal transfer arm axis is offset from the rotation axis by a transfer arm offset distance. A plurality of transfer pucks adapted to convey the parts to the substrate are attached to the distal ends of the transfer arms. Each of the transfer pucks has a longitudinal puck axis and a lateral puck axis which intersect at a center point on each of the plurality of transfer pucks. The distal ends of the transfer arms are attached to the transfer pucks at a location which is offset from the center point of the transfer pucks by a transfer puck offset distance. Each of the transfer pucks are configured to pivot between a first position wherein the transfer pucks are oriented to receive the parts and a second position wherein the transfer pucks are oriented to apply the parts to the substrate at the second position which is offset from the first position.

In yet another embodiment, the apparatus includes a plurality of transfer arms each having a longitudinal transfer arm axis, a proximal end and a distal end. The plurality of transfer arms are attached in a radial patter to a rotation means having a rotation axis. Each of the proximal ends of the transfer arms are attached to the rotation means in such a manner that the longitudinal transfer arm axis is offset from the rotation axis by a transfer arm offset distance. The apparatus also includes a plurality of transfer pucks adapted to convey the parts to the substrate. Each of the transfer pucks has a longitudinal puck axis and a lateral puck axis which intersect at a center point on each of the plurality of transfer pucks. The distal ends of the transfer arms are attached to the transfer pucks at a location which is offset from the center point by a transfer puck offset distance. Each of the transfer pucks are configured to pivot between a first position wherein the transfer pucks are oriented to receive the parts and a second position wherein the transfer pucks are oriented to apply the parts to the substrate at the second position which is offset from the first position.

Each of the transfer pucks may have a leading edge and a leading radius and a trailing edge and trailing radius with the trailing radius of one transfer puck being substantially equal to the leading radius of an adjacent transfer puck. The transfer arm offset distance may be substantially equal to the transfer puck offset distance. At least a portion of the plurality of transfer arms may be attached to at least a portion of the transfer pucks at a location which is offset from the center point along one of the longitudinal puck axis or the lateral puck axis.

In further embodiments of the invention, the apparatus may have at least a portion of the plurality of transfer arms equipped with a transfer arm adjustment means which permits selective adjustment of the transfer arm offset distance. Optionally, at least a portion of the plurality of transfer pucks may have a transfer puck adjustment means which permits selective adjustment of the transfer puck offset distance.

In variations of the present invention, the apparatus may have a first portion of the plurality of transfer pucks rotate in one direction and a second portion of the plurality of transfer pucks rotate in a second and different direction. Also, a first portion of the plurality of transfer pucks may have a first or starting position which is different from a second portion of the plurality of transfer pucks. Additionally, a first portion of the plurality of transfer pucks may have a second or ending position which is different from a second portion of the plurality of transfer pucks.

As to the offset distances, a first portion of the plurality of transfer arms may have a transfer arm offset distance which is different from a second portion of the plurality of transfer arms and a first portion of the plurality of transfer pucks may have a transfer puck offset distance which is different from a second portion of the plurality of transfer pucks. The transfer arm offset distance may from about 1 to about 70 millimeters as may be the transfer puck offset distance.

The method of the present invention involves feeding a plurality of parts at a first position into a conveying and transfer process along a supply centerline and then transferring the plurality of parts to a conveying and transfer apparatus. The conveying and transfer apparatus then rotates the plurality of parts to a second position which is offset from the supply centerline. Following this, the plurality of parts are deposited while in their second position onto the moving substrate after which the product being assembled can be subject to further processing.

DESCRIPTION OF THE DRAWINGS

A full and enabling disclosure of the present invention is set forth more particularly in the remainder of the specification, including reference to the accompanying figures, in which:

FIG. 4 is a side view of a transfer arm and transfer puck according to the present invention showing the adjustability of the transfer arm offset.

FIG. 5 is a bottom plan view of a transfer puck according to the present invention.

DETAILED DESCRIPTION

Reference will now be made in detail to present embodiments of the invention, one or more examples of which are illustrated in the accompanying drawings. Each example is provided by way of explanation of the invention and not as a limitation of the invention. In fact, it will be apparent that modifications and variations can be made in the present invention without departing from the scope or spirit thereof. For instance, features illustrated or described as part of one embodiment may be used on another embodiment to yield a still further embodiment. Additionally, parameters, measurements and elements of one example may be used alone or in combination with other parameters, measurements and elements of other examples of the present invention and may be used independently or in combination to support one or more of the claims appended hereto describing and claiming embodiments of the present invention. Thus, it is intended that the present invention covers these and other such modifications and variations as come within the scope of the appended claims and their equivalents.

Figure 1:
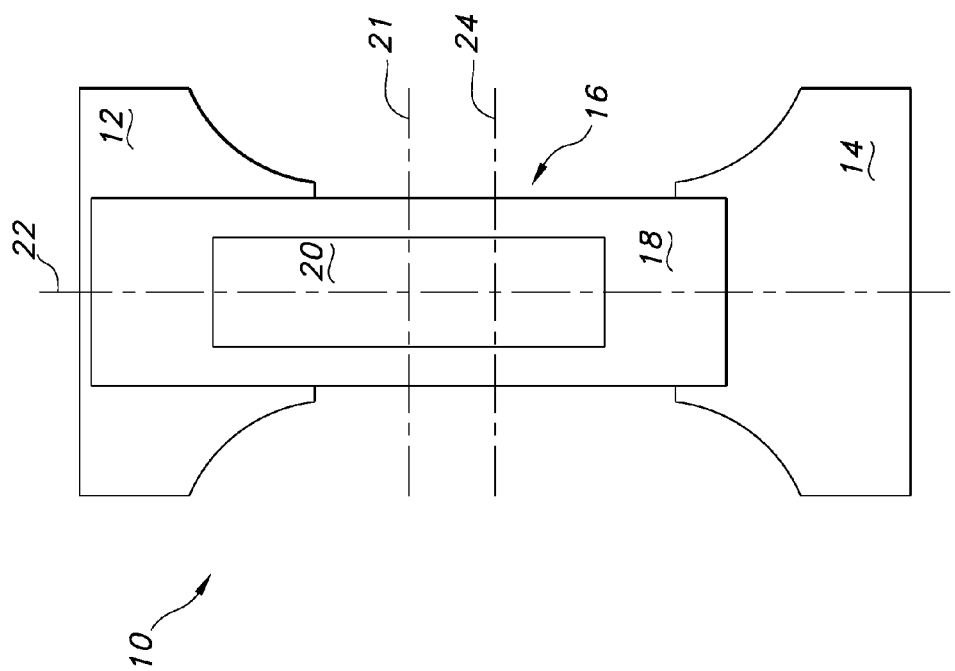
FIG. 1 is a top plan view of a personal care absorbent article, in this case an incontinent pant opened up and laid flat showing the absorbent core skewed to one end of the product.

Turning to FIG. 1 there is shown a personal care absorbent article, in this case an adult care incontinence product 10 having a front waist portion 12, a back waist portion 14 and an absorbent core assembly 16 straddling and attached to the front waist portion 12 and the back waist portion 14. The absorbent core assembly 16 includes a backing sheet 18 which is typically liquid impervious and an absorbent core 20 positioned on and attached to the backing sheet 18. As can be seen in FIG. 1, the absorbent core 20 is skewed to one end of the product 10, in this case towards the front waist portion 12. As a result, while the absorbent assembly 16 is centered on the product longitudinal centerline 22, the lateral centerline 21 of the absorbent core is offset from the product lateral centerline 24.

Figure 2:
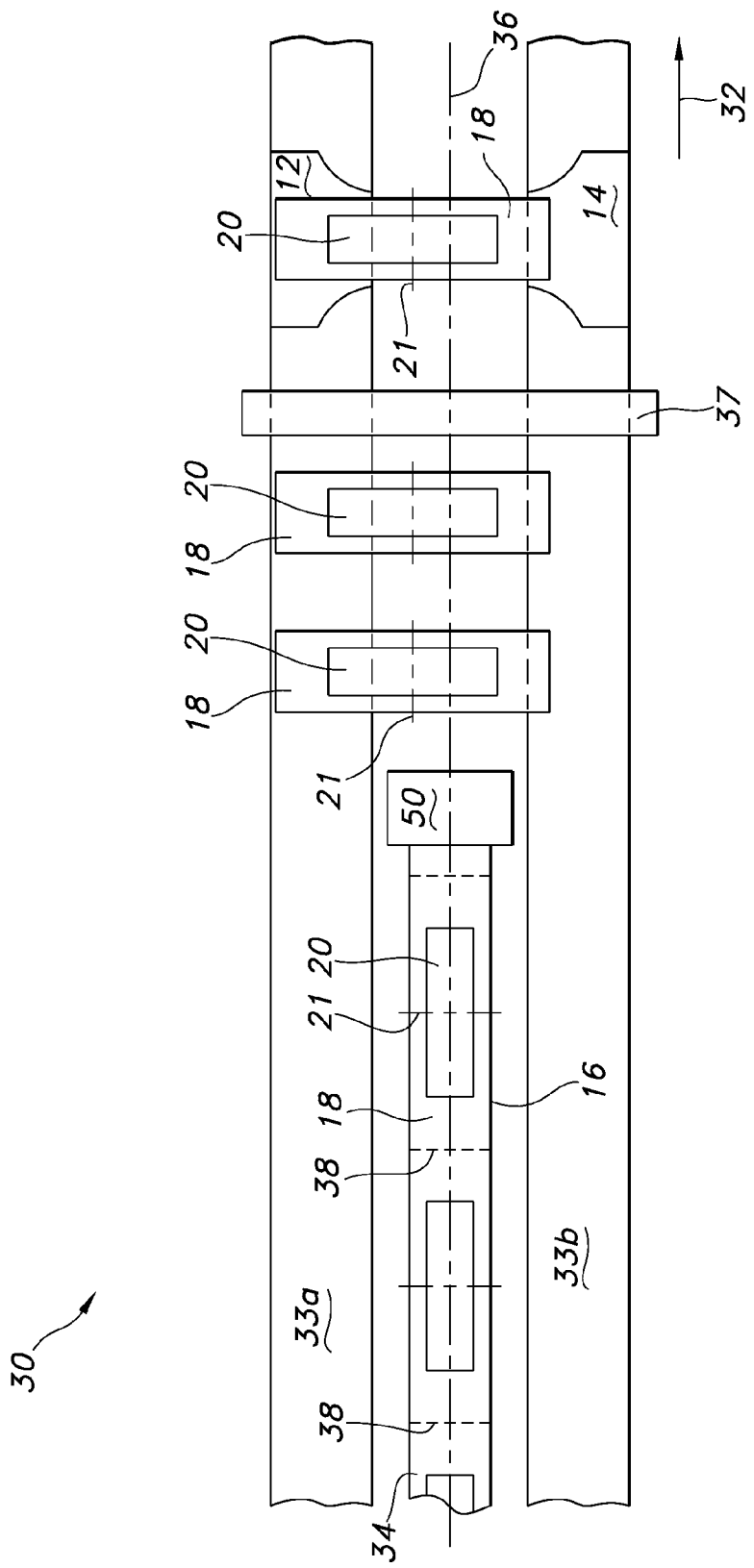
FIG. 2 is a schematic top plan view of a process configuration for making a product such as is shown in FIG. 1 utilizing the process and apparatus of the present invention.

Turning to FIG. 2, there is shown a portion of a production line 30 for forming an absorbent product 10. The line 30 moves in the direction of the arrow 32. A supply 34 of attached or interconnected absorbent assemblies 16 is shown having its longitudinal centerline centered on the production line longitudinal centerline 36. The conveying and transfer apparatus of the present invention is represented by element 50.

With conventional production lines and transfer equipment as with the present invention, the supply of parts or pieces can come into the transfer apparatus 50 in many ways. One way is for the supply 34 to be pre-cut individual pieces traveling on a carrier web, conveyor or other transportation means (not shown) which then are picked up and rotated to an offset position using the apparatus 50. A second way is for the individual pieces or assemblies 16 (as is shown in FIG. 2) to be continuously connected to one another but to have perforations 38 which are subsequently torn and separated by the action of the later described transfer arms 58 and transfer pucks 70 which form a part of the conveying and transfer apparatus 50. Yet a third way is for the individual pieces or assemblies 16 not to be separated by perforation lines but, instead, for there to be an in-line cutter mechanism (not shown) which severs the individual assemblies 16. The in-line cutter can be a part of or separate from the apparatus 50 but its function is to sever the incoming supply into individual pieces or parts just prior to the portion of the process performed by the apparatus 50 where the piece is rotated from its incoming position to its final position. Thus, in the context of the present invention including the claims, when discussing "conveying", "transferring", etc. of "pieces" or "parts" from a supply to a substrate, the supply of parts may be inputted into the apparatus in any of the above-described ways and other ways if necessary depending on the nature of the components being combined.

Turning again to FIG. 2, each of the absorbent assemblies 16 from supply 34 are separated by a perforation line 38. A supply of substrates 33a and 33b corresponding respectively to the front waist portion 12 and the back waist portion 14 are also supplied to the production line 30 and move in the direction of arrow 32. The apparatus 50 of the present invention, as will be described in further detail below, accepts the supply 34 of absorbent core assemblies 16 which are already in the machine direction and then rotates and deposits them in an offset configuration as is shown to the right of the apparatus 50 in FIG. 2 down onto substrates 33a and 33b. After the absorbent assemblies 16 are attached to the substrates 33a and 33b, the substrates are cut into the front waist portion 12 and back waist portion 14 via a conventional cutter 37 and subsequently folded and joined along their sides to form the completed pants (not shown).

Thus as to the process, it can be seen that the supply 34 of parts or pieces has its own supply centerline 36 to the left of apparatus 50 which in this case aligns with centerline of the production line 36 after the apparatus 50. It is important to note, however, that due to the operation of the apparatus 50, the lateral centerline 21 of the absorbent assembly 16 is not in alignment with the centerline 36 as would be the case with a normal rotation and transfer process that was not designed to offset the absorbent assembly 16 from the centerline 36.

Turning to FIGS. 3 through 6 there is shown schematics of a conveying and transfer apparatus 50 for conveying a plurality of parts, in this case, absorbent assemblies 16, and applying these parts 16 to substrate, which in this case is an adult care incontinence product 10. The general construction and operation of such apparatus are well known as exemplified by U.S. Pat. Nos. 5,716,478 and 5,759,340 both to Boothe et al. and 6,139,340 to Couillard et al., each of which is incorporated herein by reference in its entirety to the extent not inconsistent herewith.

As there are many ways and configurations for driving the apparatus 50 for transferring discrete parts to a substrate, for purposes of illustration, the apparatus 50 has rotation means 52 which in the figures is represented by a rotation shaft 52 defining a rotation axis 54. The rotation means 52 may be directly or indirectly driven by a drive motor or other suitable means (not shown) as is conventionally used for such transfer equipment. Thus, the rotation shaft 52 and rotation axis 54 are meant to represent the various means and methods used to propel the below-described transfer arms 58 and transfer pucks 70 in conventional equipment to which the present invention may be applied. The rotation means 52 rotates about its axis 54 in a first direction as shown by arrow 56 such that a plurality of discrete parts can be conveyed and applied to the substrate or substrates which, in this case is the front waist portion 12 and rear waste portion 14. Note too, however, that due to the variability of conventional conveying equipment designs with which the present invention may be used, it is also possible that the rotation axis 54 may not coincide with the rotation means 52 as there may be intermediate drive equipment used which thus indirectly causes the below-describes transfer arms 58 and transfer pucks 70 to have a separate rotation axis 54 from the main drive axis of the equipment.

Connected to the rotation means 52 are a plurality of transfer arms 58 which are attached to the rotation means 52 in a radial pattern. Each of the transfer arms 58 has a proximal end 60 attached directly or indirectly to the rotation means 52 and a distal end 62 attached to a transfer puck 70. Each of the transfer arms 58 has a longitudinal transfer arm axis 64 which is offset from and perpendicular to the rotation axis 54 of the rotation means 52. The longitudinal transfer arm axis 64 runs through the point at which the distal end 62 of the transfer arm 58 is attached to the transfer puck 70 and is generally perpendicular to the plane in which the transfer puck 70 resides. Each transfer arm 58 has a transfer arm offset distance 66, the distance "x" of which is the distance between the rotation axis 54 and the longitudinal transfer arm axis 64. See FIG. 4. When the apparatus 50 according to the present invention is being used to form personal care absorbent articles, it has been found that it is desirable for the transfer arm offset distance 66 to be from about 1 to about 70 millimeters, more desirably between about 1 and about 50 millimeters and most desirably between about 1 and about 30 millimeters.

As mentioned above, each of the plurality of transfer arms 58 has a transfer puck 70 attached to the distal ends 62 of the respective transfer arms 58. Each of the transfer pucks 70 is equipped with conventional vacuum assist or other means (not shown) to allow the transfer puck 70 to pick up discrete pieces of material as is the case with conventional non-offset transfer equipment. Turning to FIG. 5, each of the plurality of transfer pucks 70 can have a longitudinal transfer puck axis 72 and a lateral transfer puck axis 74 which intersect at a center point 76. The center point 76 would be the normal point of attachment of the transfer arm 58 to the transfer puck 70 in conventional non-offset equipment. To facilitate the ability of the apparatus 50 to convey discrete pieces to a substrate at an offset from the normal centerline of the conveyor system and the products or substrates traveling down it, the distal ends 62 of the transfer arms 58 are attached to the transfer pucks 70 at a point which is offset from the center point 76 of the transfer pucks 70. See FIGS. 3 and 4.

Generally, it is desirable that the distal ends 62 of the transfer arms 58 be connected to and offset from the center points 76 of the transfer pucks 70 by a transfer puck offset distance 78. The transfer puck offset distance 78, the distance "y", is the distance between the longitudinal transfer arm axis 64 of the transfer arm 58 and the center point 76 of the transfer puck 70. When the apparatus 50 according to the present invention is being used to form personal care absorbent articles, desirably the transfer puck offset distance 78 is from about 1 to about 70 millimeters, more desirably between about 1 and about 50 millimeters and most desirably between about 1 and about 30 millimeters.

In most instances it is desirable that the transfer arm offset distance 66 and the transfer puck offset distance 78 be equal. However, in some instances they may be different and in other instances it is acceptable that distances "x" and "y" be substantially the same, "substantially" meaning that the values of x and y vary by no more than twenty (20) percent of one another.

The point at which the distal ends 62 of the transfer arms 58 are attached to the transfer pucks 70 can be at any point on the transfer pucks 70 to create the desired degree of offset distance. Normally, however, the point of attachment will likely lie along either the longitudinal transfer puck axis 72 or the lateral transfer puck axis 74 depending on the size and shape of the part being transferred and the beginning and ending orientation/rotation of the part.

Each of the transfer pucks 70 are configured using conventional means to pivot about the longitudinal transfer arm axes 64 so that each of the transfer pucks 70 are pivotal between a first position 80 wherein the transfer pucks 70 are oriented to receive the parts and a second position 82 wherein the transfer pucks 70 are oriented to apply the parts to the substrate. See FIG. 3.

Referring to FIG. 4, relative to the direction of rotation 56, each of the transfer pucks 70 has a leading edge 84 and a leading radius 86 and each of the transfer pucks 70 has a trailing edge 88 and a trailing radius 90. The leading radius 84 is the distance between the rotation axis 54 and the point at which the radial line 86 intersects the outermost portion of the leading edge 84 of the transfer puck 70. Similarly, the trailing radius 90 is the distance between the rotation axis 54 and the point at which the radial line 90 intersects the outermost portion of the trailing edge 88 of the transfer puck 70. If there is too great a disparity in the radial distances between the trailing edge 88 of one transfer puck 70 and the leading edge 84 of an adjacent transfer puck 70 relative to the rotation axis 54, problems can arise in maintaining consistent feeding of the discrete parts into the assembly line, especially when they are attached to one another and require the breaking of a perforation line 38 of the supply 34 as is shown in FIG. 2. The disparity of radial distances of the adjacent leading 84 and trailing 88 edges can cause the perforations 38 to prematurely tear thereby disrupting the operation of the production line and necessitating stopping the apparatus to rethread the supply 34 of absorbent assemblies 16. As a result, it is desirable that the leading radius 86 and the trailing radius 90 of adjacent transfer pucks 70 be substantially equal, "substantial" meaning that the values vary by no more than twenty (20) percent of one another. Maintaining this tolerance can be the result of adjusting either or both of the transfer arm offset distance 66 and the transfer puck offset distance 78.

Figure 3:
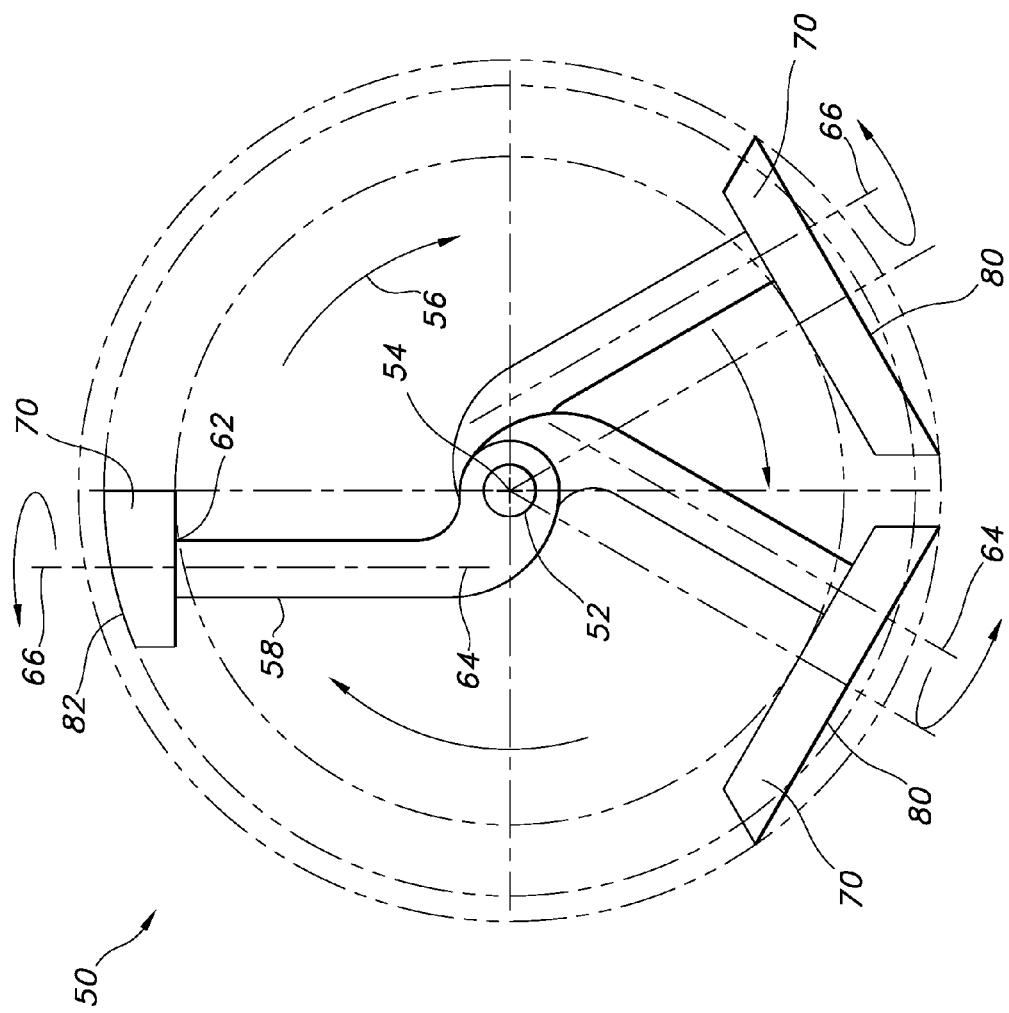
FIG. 3 is a side view of an apparatus according to the present invention.

In FIG. 3, the transfer arms 58 are shown formed to have a constant transfer offset distance "x". In order to create the proper amount of offset of the apparatus 50 to cause proper transfer of the discrete parts to the substrate and to create greater flexibility in the operation of the apparatus 50, one or all of the transfer arms 58 can be equipped with an optional transfer arm adjustment means 92 which permits selective adjustment of the transfer arm offset distance "x". As shown in FIG. 4, the transfer arm adjustment means 92 comprises a plurality of shims which may be added or deleted to increase or decrease the transfer arm offset distance "x". The shims can be as simple as a plurality of sized washers fitted onto a bolt or other securement means 94 which can be used to adjustably secure the transfer arm 58 to the rotation means 52.

In the same fashion, one or all of the transfer pucks 70 can be equipped with an optional transfer puck adjustment means 96 which permits selective adjustment of the transfer puck offset distance "y". As shown in FIG. 5, to create the transfer puck adjustment means 96, the transfer pucks 70 may be provided with a plurality of attachment points which may or may not be designed to selectively match increases or decreases in the transfer arm offset distance "x".

While it is generally desirable that the transfer arms 58 and transfer pucks 70 operate in the same way, it is also possible to vary the operation of one portion of the apparatus 50 from a second portion of the apparatus 50. For example, while the apparatus 50 according to the present invention has been described in conjunction with the formation of an incontinence product, the apparatus 50 can be used for the production of any type of personal care absorbent article including, but not limited to, infant and adult diapers, training pants, diaper pants and incontinence devices such as male guards and liners. In the context of feminine hygiene products, the apparatus 50 according to the present invention can be used to produce sanitary napkins, sanitary pants, panty liners and tampons. Furthermore, the apparatus 50 and method of operation according to the present invention can be used in any assembly process where it is desired to create offsets in the placements of one work piece in connection with another. For example, it may be desirable to have the apparatus 50 apply discrete pieces with offsets in one direction for one portion of the production cycle and offsets in one or more other directions for other portions of the production cycle. As a result, it is possible for there to be a first portion of the transfer pucks 70 which rotate in one direction and a second portion of the transfer pucks 70 which rotate in a second and different direction.

Normally, the apparatus 50 is designed to rotate pieces from a first position to a second position which is 90 degrees different from the first position. However, in other embodiments, it is within the scope of the present invention to have a first portion of the plurality of transfer pucks 70 have a first or starting position which is different from a second portion of the plurality of transfer pucks 70. Alternatively, it is within the scope of the present invention to have a first portion of the plurality of transfer pucks 70 have a second or finishing position 82 which is different from a second portion of the plurality of transfer pucks 70. It is still a further possibility, consistent with the scope of the present invention, to have still further combinations of first and second positions (80 and 82) for individual transfer pucks 70 on the same apparatus 50.

The same is also true with respect to the offsets of both the transfer arms 58 and the transfer pucks 70. A first portion of the plurality of transfer arms 58 may have a transfer arm offset distance 66 which is different from a second portion of the plurality of transfer arms 58. A first portion of the plurality of transfer pucks 70 may have a transfer puck offset distance 78 which is different from a second portion of the plurality of transfer pucks 70. It is still a further possibility consistent with the scope of the present invention to have still further combinations of first and second positions for individual transfer arms 58 and transfer pucks 70 on the same apparatus 50.

As stated previously, there are many designs of equipment and processes with which the present invention can be employed. In many designs there are physical transfer arms 58 such as depicted with respect to the apparatus 50 shown in FIG. 3. Thus, in the context of the present invention, the transfer arms 58 are meant to represent any means (both as to equipment and process) used to convey and rotate the transfer pucks 70.

Figure 6:
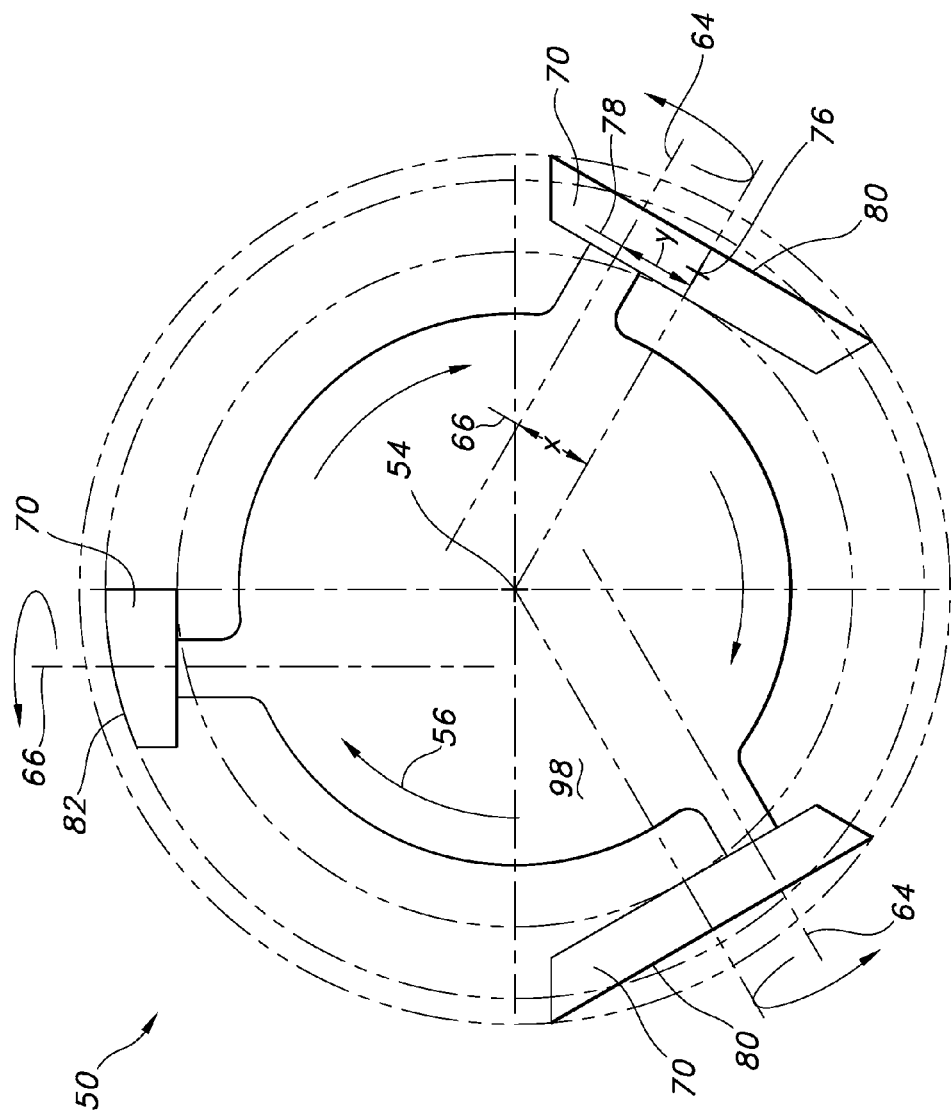
FIG. 6 is a side view of an alternate apparatus construction according to the present invention.

Illustrating this point is another embodiment of the present invention shown in FIG. 6. In this embodiment, like elements are numbered in a like manner the exception being that the apparatus 50 is supplied with a transfer disk 98 which is in lieu of the transfer arms 58. As can be seen from the figure, the equivalent of the transfer arm axis 64 is still present as is the offset 66 of this axis 64 from rotation axis 54 and the offset 78 of the transfer puck 70. In this design as with the other design, the pivot point of the transfer puck 70 is offset from what would be the normal pivot point if the center point 76 of the transfer puck 70 was in line with the rotation axis 54.

Thus, having described the conveying and transfer apparatus 50, it can be seen that the conveying and transfer process 30 shown in FIG. 2 of the drawings provides a method for applying a plurality of parts to a moving substrate. The parts, which in this case are the absorbent assemblies 16, are fed into the apparatus 50 as a supply 34 which has a supply centerline 36. As shown in FIG. 2, the absorbent assemblies 16 are in a first position. As the supply 34 of assemblies enter the apparatus 50, the individual transfer pucks 70 are spaced to pick up the assemblies 16 at a first position which corresponds to transfer puck first position 80. As the transfer pucks 70 are sped up (using conventional technology), the perforation lines 38 separate so that each transfer puck 70 is carrying its own discrete part. The transfer puck 70 then rotates from its first position 80 to its second position 82 (which is this case is orthogonal to the incoming position) and thus causes the parts (absorbent assemblies 16) to move to a second position. The transfer pucks 70 then deposit the individual parts (absorbent assemblies 16) in their second position which is offset from the supply centerline 36 down onto the moving substrates 33*a* and 33*b* (respectively front waist portion 12 and rear waist portion 14). Once the absorbent assemblies 16 are attached to the front and rear waist portions (12 and 14), a conventional cutter 37 is used to cut the combined components into individual products 10 as shown in FIG. 1. The products 10 in subsequent conventional processing steps not shown are folded and the front and back waist portions (12 and 14) are joined to one another to form a finish product.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. An apparatus for conveying a plurality of parts and applying said parts to a substrate, the apparatus comprising:
   a rotation means defining a rotation axis, said rotation means having a first direction of rotation about said rotation axis such that said plurality of parts can be applied to said substrate;
   a plurality of transfer arms each having a longitudinal transfer arm axis, a proximal end and a distal end, said plurality of transfer arms being attached to said rotation means in a radial pattern about said rotation means each of said proximal ends of said transfer arms being attached to said rotation means in such a manner that said longitudinal transfer arm axis is offset from said rotation axis by a transfer arm offset distance; and
   a plurality of transfer pucks adapted to convey said parts to said substrate, each of said transfer pucks having a longitudinal puck axis and a lateral puck axis which intersect at a center point on each of said plurality of transfer pucks, said distal ends of said transfer arms being attached to said transfer pucks at a location which is offset from said center point by a transfer puck offset distance,
   each of said transfer pucks has a leading edge and a leading radius and a trailing edge and trailing radius wherein said trailing radius of one transfer puck is substantially equal to the leading radius of an adjacent transfer puck,
   each of said transfer pucks being configured to pivot about said longitudinal transfer arm axis so that each of said transfer pucks is pivotal between a first position wherein said transfer pucks are oriented to receive said parts and second position wherein said transfer pucks are oriented to apply said parts to said substrate.

2. The apparatus of claim 1 wherein said transfer arm offset distance is substantially equal to said transfer puck offset distance.

3. The apparatus of claim 1 wherein at least a portion of said plurality of transfer arms have a transfer arm adjustment means which permits selective adjustment of said transfer arm offset distance.

4. The apparatus of claim 1 wherein at least a portion of said plurality of transfer pucks have a transfer puck adjustment means which permits selective adjustment of said transfer puck offset distance.

5. The apparatus of claim 1 wherein a first portion of said plurality of transfer pucks rotate in one direction and a second portion of said plurality of transfer pucks rotate in a second and different direction.

6. The apparatus of claim 1 wherein a first portion of said plurality of transfer pucks have a first position which is different from a second portion of said plurality of transfer pucks.

7. The apparatus of claim 1 wherein a first portion of said plurality of transfer pucks have a second position which is different from a second portion of said plurality of transfer pucks.

8. The apparatus of claim 1 wherein a first portion of said plurality of transfer arms have a transfer arm offset distance which is different from a second portion of said plurality of transfer arms.

9. The apparatus of claim 1 wherein a first portion of said plurality of transfer pucks have a transfer puck offset distance which is different from a second portion of said plurality of transfer pucks.

10. The apparatus of claim 1 where said transfer arm offset distance is from about 1 to about 70 millimeters.

11. The apparatus of claim 1 where said transfer puck offset distance is from about 1 to about 70 millimeters.

12. The apparatus of claim 1 wherein at least a portion of said plurality of transfer arms are attached to at least a portion of said transfer pucks at a location which is offset from said center point along one of said longitudinal puck axis or said lateral puck axis.

* * * * *